United States Patent

Cross

[11] 3,988,300
[45] Oct. 26, 1976

[54] BENZOPHENONE UREAS AND METHOD FOR UTILIZING THE SAME

[75] Inventor: Barrington Cross, Rocky Hill, N.J.

[73] Assignee: American Cyanamid Company, Stamford, Conn.

[22] Filed: May 31, 1973

[21] Appl. No.: 365,807

[52] U.S. Cl. .............................. 260/553 A; 71/88; 71/94; 71/120; 260/247.2 A; 260/293.77; 260/453 R; 260/554; 260/570 AB; 260/453 AR; 260/453 AM
[51] Int. Cl.² .............. C07C 127/19; C07C 127/15; C07D 211/06; C07D 295/00
[58] Field of Search .......... 260/553 A, 554; 71/103, 71/120

[56] References Cited
UNITED STATES PATENTS

| | | | |
|---|---|---|---|
| 2,885,435 | 5/1959 | Pursglove | 71/103 X |
| 2,927,126 | 3/1960 | Pursglove | 71/103 X |
| 3,060,235 | 10/1962 | Martin et al. | 260/553 A |
| 3,119,682 | 1/1964 | Martin et al. | 260/553 A X |
| 3,707,557 | 12/1972 | Brown | 260/553 A |
| 3,775,444 | 11/1973 | Jensen et al. | 260/553 A X |
| 3,910,911 | 10/1975 | Ishizumi et al. | 260/553 A X |

FOREIGN PATENTS OR APPLICATIONS

| | | | |
|---|---|---|---|
| 44,371 | 4/1966 | Germany | 260/553 A |
| 29,756 | 7/1971 | Japan | 71/120 |

OTHER PUBLICATIONS
CA 72; 43206a (1970).
CA 73: 98650s (1970).
CA 72: 43605e (1970).

*Primary Examiner*—Floyd D. Higel
*Assistant Examiner*—Thomas A. Waltz
*Attorney, Agent, or Firm*—Harry H. Kline

[57] ABSTRACT

This invention provides for novel benzophenone ureas, a method for preparing the same, and a method for controlling undesirable broadleaf weeds and grasses therewith, wherein said benzophenone is represented by the generic formula:

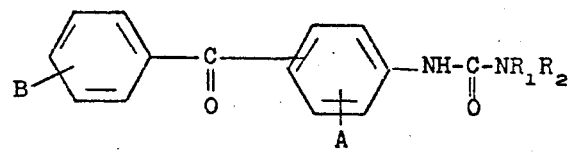

where A and B each represent hydrogen, methyl, halogen, trifluoromethyl, or methoxy; $R_1$ and $R_2$ are taken singly or in combination and represent hydrogen, lower alkyl, alkoxy, alkoxyalkyl, cycloalkyl, cyclohetero, loweralkylamino, lower alkenyl or lower alkynyl, with the proviso that A is either meta or para to the $-HN-CO-NR_1R_2$ substituent.

5 Claims, No Drawings

BENZOPHENONE UREAS AND METHOD FOR UTILIZING THE SAME

The present invention relates to novel benzophenone ureas having the formula:

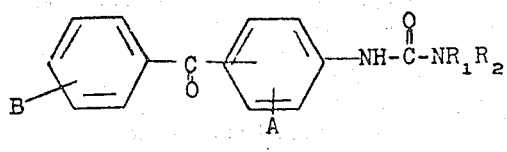

where A and B represent a member selected from the group consisting of hydrogen, methyl, halogen, trifluoromethyl, and methoxy; $R_1$ and $R_2$ each represent a member selected from the group consisting of hydrogen, loweralkyl $C_1$-$C_4$, alkoxy $C_1$-$C_4$, alkoxyalkyl $C_2$-$C_6$, cycloalkyl $C_3$-$C_6$, cyclohetero, loweralkylamino $C_1$-$C_4$, loweralkenyl $C_2$-$C_4$, and loweralkynyl $C_2$-$C_4$; and providing that the substituent represented by A is meta or para to the —NH—CO—$NR_1R_2$ substituent. The invention further relates to a process for preparing the said ureas. Still further, this invention relates to a method for controlling undesirable broadleaf weeds and grasses, utilizing the compounds of the ureas above-identified.

In accordance with the process of invention, benzoylphenyl ureas (I) may be prepared by a procedure involving the use of an appropriate aminobenzophenone (II).

As one embodiment of the invention, hereinafter termed embodiment (A), phosgene is passed through a solution of an aminobenzophenone (II) in an aprotic solvent, such as benzene, toluene, or xylene, in the presence of a molar equivalent of anhydrous alkali metal carbonate, such as sodium or potassium carbonate. Reaction temperature is generally maintained at between about 40° and 100° C., although somewhat higher or lower temperature may be used. After removal of excess phosgene, an appropriate amine ($NHR_1R_2$) in an aprotic solvent (e.g., benzene) is added at about 0° C. to 20° C. to resultant so-formed benzophenone isocyanate. In such reaction the intermediate, i.e., the benzophenone, is preferably in the same aprotic solvent. Usually, the desired product precipitates and is filtered off. Crystallization is often necessary from benzene in order to remove insoluble impurities, such as carbanilide.

Graphically, the process of the invention may be illustrated in the following manner:

(1)

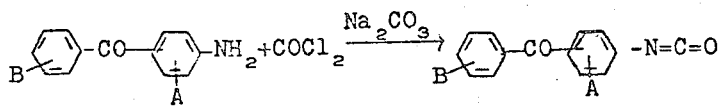

and (2)

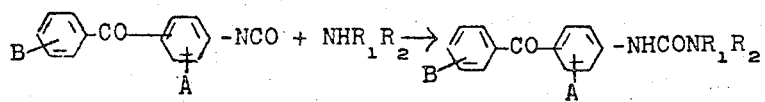

where A, B, $R_1$ and $R_2$ are the same as defined above.

In an alternative embodiment of the present invention, hereinafter termed embodiment (B), a substituted carbamoyl chloride is reacted with an aminobenzophenone (II) above in the presence of a base, such as triethylamine, pyridine, sodium carbonate, potassium carbonate, sodium bicarbonate, and a solvent, such as acetone, ether, or dimethylformamide. The reaction mixture is heated to between about 50° and 80° C., and preferably between 50° and 60° C., to effect reaction.

In general, the reaction may be illustrated as follows, wherein A, B, $R_1$ and $R_2$, are defined above.

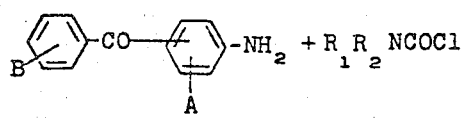

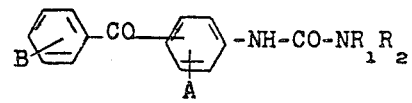

Advantageously, the compounds of the invention can also be prepared by a third embodiment (C), which involves reaction of the aminobenzophenone (II) with the appropriate substituted isocyanate in an aprotic solvent. This process is particularly effective for the preparation of monoalkylureas, since it provides such compounds in high yield. The reaction may be graphically illustrated as follows wherein A, B, and $R_1$ are as defined above.

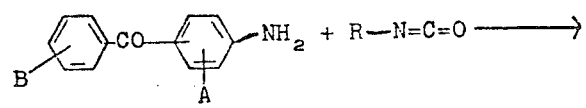

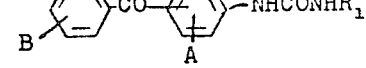

Illustrative aminobenzophenone reactants are: 4-aminobenzophenone, 4-amino-4'-chloro-2-methoxybenzophenone; 4-amino-2,4'-dichlorobenzophenone; 4-amino-2-chloro-4'-methoxybenzophenone; 4-amino-2,4'-dibromobenzophenone; 4-amino-2,4-dimethylbenzophenone; 4-amino-4'-trifluoromethylbenzophenone; 4-amino-4'-methylbenzophenone; 4-amino-4'-methoxybenzophenone; 4-amino-2,3'-dichlorobenzophenone; 5-amino-2-chlorobenzophenone; 5-amino-2-bromobenzophenone; 5-amino-2,4'-dichlorobenzophenone; 5-amino-2,4'-dibromobenzophenone; 5-amino-2,3'-dimethylbenzophenone; and 4-amino-2-chlorobenzophenone.

In general, the aminobenzophenones are initially obtained by the reduction of nitrobenzophenone. For instance, one reduction method involves the use of metal acid reduction as exemplified by iron and hydrochloric acid conducted in an ethanol-water medium. Other metal-reducing agents are similarly suitable, as for instance, tin, stannous chloride, zinc, and other weak or strong mineral or organic acids, such as acetic acid or nitric acid. Solvents miscible with water, such as alcohols or even acetic acid may be used. Further, alkaline reducing conditions are also suitable; e.g., sodium dithionite in water, or zinc in aqueous alkali. Another method is the use of catalytic reduction employing hydrogen and catalysts, such as Raney nickel, ruthenium on carbon, palladium on carbon, or platinum oxide in an alcoholic medium. The latter catalysts prevent dehydrohalogenation.

The nitrobenzophenones employed above can be prepared by a Friedel-Crafts benzoylation of a substituted benzene in the presence of at least a molar excess of aluminum chloride, hydrogen fluoride or boron trifluoride.

The overall reaction including the reduction stage to obtain an aminobenzophenone where A and B are as defined above can be written as follows:

1)

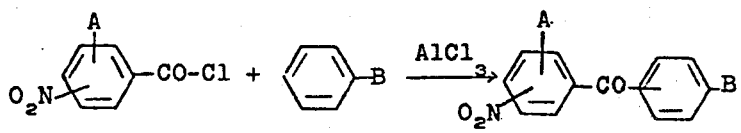

and

2)

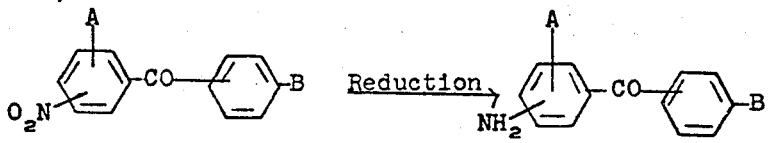

Advantageously, the compounds of the invention can be formulated in conventional type formulations; such as dusts, dust concentrates, wettable powders, liquid concentrates, or granular formulations.

The wettable powder formulations may be prepared by grinding together from about 25 to 75% by weight of the active benzophenone urea with about 23 to 73% by weight of a finely divided solid diluent; such as attapulgite, bentonite, kaolin, talc, diatomaceous earth, or pumice, and admixing therewith from about 1% to 5% by weight of an anionic-nonionic emulsifier and/or from about 1% to 5% by weight of a dispersing agent. A typical anionic-nonionic blend which may be used contains the calcium salt of myristylbenzene sulfonic acid and the oleate ester of a polyoxyethylene glycol (molecular weight = 350) in a 3 to 1 ratio. Also useful is the blend of calcium laurylpheno-sulfonic acid and polyoxyethylene sorbitan monolaurate. Dispersing agents which may be used in these formulations include the mono-calcium salt of a polymerized alkylaryl sulfonic acid, the sodium salt of condensed naphthylene sulfonic acid, the alkali metal lignosulfonates.

Liquid concentrates may be prepared by dissolving from about 25 to 75% by weight of the benzophenone urea in from about 73 to 23% by weight of an organic solvent, benzenes, toluene, xylene, and mixtures thereof, ketones (such as acetone, methylethylketone, or methylisobutylketone), or alcohols (such as methanol, ethanol, isopropanol, n-butanol or hexanol). Generally, from about 2% to 5% by weight of an emulsifier, such as named above, is also included in such formulations. Spreaders, stickers, surface active agents and the like, may also be added when desired.

In practice, these wettable powder and liquid concentrate formulations are usually dispersed in water and/or some other relatively inexpensive diluent and applied to the soil containing seeds or seedling plants of undesirable broad leaf weeds and/or grasses or the foliage of such plants to control the same.

For preemergence control of undesirable plants generally about 1 to 25 pounds of the active compounds per acre, is effective, whereas, application of such compounds as postemergence herbicidal agents usually requires only about 1/8 pound to 15 pounds, and preferably one eighth pound to 10 pounds per acre of the inventive compounds for effective weed and grass control.

Granular formulations, which are prepared by coating the surfaces of an inert carrier; such as ground corn cobs, sand, clay, or similar particles, with from about 5 to 25% by weight, and preferably 10 to 15% by weight of the active benzophenone urea and particularly useful for preemergence weed and grass control. These formulations lend themselves to preplant incorporation techniques or to soil surface application.

The invention will be further illustrated in detail by the following specific examples. It should be understood, however, that although these examples may describe some of the more specific features of the invention, they are given primarily for purposes of illustration, the invention in its broader aspects is not to be construed as being limited thereto. Unless otherwise specified, the parts and percentages are by weight.

EXAMPLE 1

Preparation of
3-[3-Chloro-4-(p-chlorobenzoyl)phenyl]-1,1-dimethyl Urea, Employing Procedure A Above In a suitable reaction vessel was added anhydrous sodium carbonate (3.6 grams, 0.034 mole) to 3-chloro-4-(p-chlorobenzoyl)aniline (9 grams, 0.034 mole) suspended in toluene (350 ml.). Phosgene was then bubbled through the solution for an additional one and one-half hours. After cooling the reaction mixture, it was filtered and evaporated to recover a syrupy oil, 3-chloro-4-(p-chlorobenzoyl)phenylisocyanate. Dry benzene (200 ml.) was added to the syrup, and then with stirring, dimethylamine (10 grams) in benzene (100 ml.) was added. A white solid 3-[3-chloro-4-chlorobenzoyl)phenyl]-1,1-dimethyl urea, was precipitated and filtered off. There were recovered 10.2 grams of product amounting to a 88% yield and having a melting point equal to 170° – 172° C. Crystallization from benzene gave colorless plates possessing a melting point equal to 173° – 174° C.

On Analysis in percent: Calculated for $C_{16}H_{14}N_2O_2Cl_2$: C, 56.99; H, 4.18; N, 8.31; Cl, 21.03. Found: C, 57.01; H, 3.81; N, 8.19; Cl, 20.95.

EXAMPLE 2

Preparation of 3-(m-Benzoylphenyl)-1,1-dimethyl Urea Employing Procedure B Above Dimethylcarbamoyl chloride (7.5 grams, 0.07 mole) was added to a solution of 3-aminobenzophenone (10 grams, 0.05 mole) in dimethylformamide (150 ml.), triethylamine (10 ml.) at 10° C. with stirring and ice cooling. The reaction temperature was next raised to 60° C. for 20 hours, then cooled and poured onto ice water (500 grams) containing dilute hydrochloric acid. A tarry solid was obtained by decanting off the aqueous organic solution. Purification was effected by dissolving the tarry solid in methylene chloride and passing through a silica gel dry column eluant methylene chloride. On elution with dichloromethane, the product, 3-(m-benzoylphenyl)-1,1-dimethyl urea, is obtained. Melting point was 104° –105° C. Crystallization from benzene-hexane (9:1) mixture gave solid 109° – 110° C., which on benzene-hexane crystallizations afforded a melting point of from 121° to 122° C. identified as the desired urea by comparison with the sample prepared from phosgene and dimethylamine.

Analysis Calculated for $C_{16}H_{16}N_2O_2$: C, 71.6; H, 6.0; N, 10.4. Found: C, 71.9; H, 6.24; N, 10.3.

EXAMPLES 3 - 21

In the examples which follow, aminobenzophenones are reacted in accordance with Procedures A, B, or C outlined above to yield the structures which are characterized and summarized in Table I below.

TABLE I

| Ex. No. | Structure | Procedure | Reaction Solvent | Conditions | (%) Yield | Melting Point °C | Analysis (%) Calculated | Found |
|---|---|---|---|---|---|---|---|---|
| 3 | ⟨⟩—CO—⟨⟩—NH—CO—N(CH₃)₂ | A | toluene | 50° C. 2 hours COCl₂ | 30 | 144.5–145° | C,71.6 H,6.0 N,10.4 | C,71.6 H,6.1 N,10.6 |
| 4 | ⟨⟩CO⟨⟩—NH—CO—NHCH₃ | C | dimethylformamide | 70° C. 16 hours (trace pyridine) | 28 | 215–216° | C,70.9 H,5.6 N,11.0 | C,70.7 H,5.3 N,11.0 |
| 5 | ⟨⟩—CO—⟨⟩ NH—CO—N(CH₃)₂ | B | dimethylformamide | triethylamine at 60° C | 5 | 121–122° | C,71.6 H,6.0 N,10.4 | C,71.9 H,6.1 N,10.4 |
|  |  | A | toluene | 50° C. 3 hours COCl₂ | 53 | 123.5–125° |  | C,71.5 H,6.0 N,10.2 |
| 6 | ⟨⟩—CO—⟨⟩—NH—C—N(CH₃)₂ Cl | A | toluene | 90° C. | 84 | 166.5–167° | C,63.5 H,5.0 N,9.3 Cl,11.7 | C,63.4 H,4.4 N,9.0 Cl,12.0 |
| 7 | Cl—⟨⟩—CO—⟨⟩—NH—CO—N(CH₃)₂ Cl | A | toluene | 98° C. 1.5 hours COCl₂ | 72 | 173–174° | C,57.0 H,4.2 N,8.3 Cl,21.0 | C,57.0 H,3.8 N,8.2 Cl,21.0 |
| 8 | Cl—⟨⟩—CO—⟨⟩—NH—CO—N(CH₃)₂ | A | toluene | 95° C. 1.5 hours COCl₂ | 56 | 197–197.5° | C,63.5 H,5.0 N,9.3 Cl,11.7 | C,63.4 H,4.9 N,9.0 Cl,11.7 |

TABLE I-continued

| Ex. No. | Structure | Procedure | Reaction Solvent | Conditions | (%) Yield | Melting Point °C | Analysis (%) Calculated | Found |
|---|---|---|---|---|---|---|---|---|
| 9 | 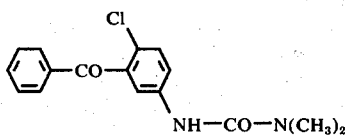 | A | toluene | 92° C. 2 hours COCl₂ | 14 | 137–138° | C,63.5 H,5.0 N,9.3 Cl,11.7 | |
| 10 | 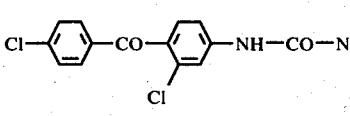 | A | benzene | (CH₃)₃C—NH₂ | 60 | 142–144° | C,59,19 H,4.96 N,7.67 Cl,19.41 | C,58.98 H,5.14 N,6.94 Cl,19.24 |
| 11 | 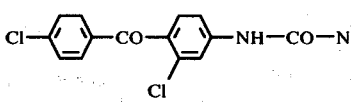 | A | benzene | ▷—NH₂ | 66 | 160.5–161.5° | C,58.47 H,4.04 N,8.02 Cl,20.30 | C,58.44 H,3.46 N,7.44 Cl,20.19 |
| 12 | 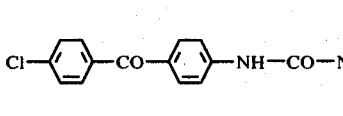 | A | benzene |  | 67 | 158–159° | C,60.48 H,4.80 N,7.42 Cl,18.79 | C,60.79 H,4.84 N,7.46 Cl,18.83 |
| 13 | 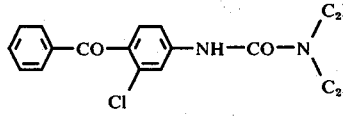 | A | benzene | (H₅C₂)₂NH | 30 | 194–195° | C,65.33 H,5.86 N,8.47 Cl,10.72 | C,65.81 H,5.83 N,8.27 Cl,10.88 |
| 14 | 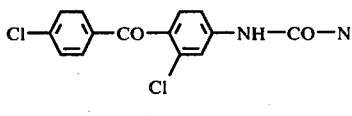 | A | benzene | CH≡CH₂—NH₂ | 30 | 183–184° | C,58.80 H,3.50 N,7.89 Cl,20.42 | C,59.13 H,3.41 N,7.81 Cl,20.41 |
| 15 | 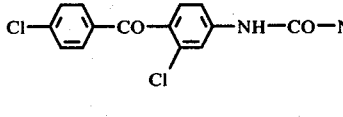 | A | benzene | 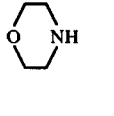 | 43 | 144.5–146° | C,57.00 H,4.22 N,7.38 Cl,18.69 | C,56.98 H,4.00 N,7.01 Cl,18.84 |
| 16 | 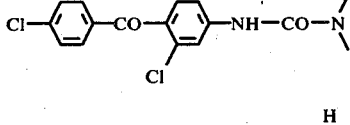 | A | benzene | H₅C₂O—(CH₂)₂NH₂ | 60 | 124.5–126° | C,56.70 H,4.75 N,7.35 Cl,18.59 | C,56.49 H,4.12 N,6.94 Cl,18.49 |
| 17 | 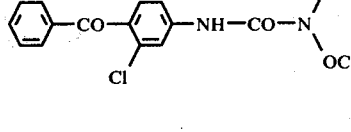 | A | benzene | CH₃O—NH₂ | 23 | 151.5–152.5° | C,59.26 H,4.30 N,9.20 Cl,11.63 | C,59.79 H,4.40 N,8.40 Cl, — |
| 18 | 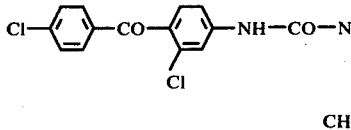 | A | benzene | (CH₂=C—CH₂—)NH | — | oil | C,61.73 H,4.66 N,7.20 Cl,18.23 | C,61.86 H,4.57 N,6.90 Cl, — |
| 19 | 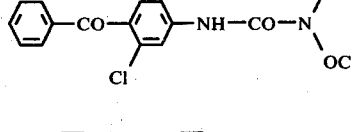 | * | methanol-water | (CH₃)₂SO₄ | 84–86.5° | C,60.3 H,4.7 N,8.80 Cl,11.13 | C,61.0 H,4.8 N,9.0 Cl,11.5 | |
| 20 | 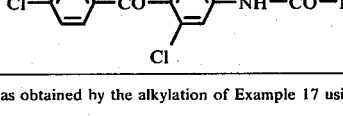 | A | benzene | (CH₃)₂—N—NH₂ | 37 | 152.5–153° | C,54.58 H,4.29 N,11.93 Cl,20.14 | C,55.06 H,4.03 N,11.40 Cl,20.48 |

*19 was obtained by the alkylation of Example 17 using dimethylsulfate in methanolic alkali.

EXAMPLE 21

Preparation of 2-Chloro-4-nitrobenzophenone Intermediate

Thionyl chloride (35.8 grams, 0.305 mole) was added to a benzene solution of 2-chloro-4-nitrobenzoic acid (60.3 grams, 0.3 mole) and the mixture heated to reflux during 5 hours until the evolution of hydrogen chloride had ceased. Aluminum chloride (100 grams, 0.72 mole) was added slowly to the stirred solution during a 3.5 hour period and the temperature rose to 48° C. After the addition, the mixture was warmed to 80° C. for 2 hours, cooled, poured onto ice-water (one liter), concentrated hydrochloric acid (90 ml.) added and the mixture warmed at 40° C. for 3 hours. Benzene extraction followed by successive treatment with 5% aqueous sodium hydroxide, water and calcium chloride yielded, after removal of benzene, a reddish black residue purified by filtration. The pale yellow solid so obtained was further characterized as having a melting point equal to 95.5° – 96.5° C. in 44% yields.

EXAMPLE 22

Repeating Example 21 in every detail except that a chlorobenzene solution of 2-chloro-4-nitrobenzoic acid was employed in lieu of the benzene solution of the same, there is obtained a 50% yield of 2,4′-dichloro-4-nitrobenzophenone in good yield and purity having a melting point of 117° – 117.5° C.

EXAMPLE 23

The procedure of Example 21 is repeated in every detail except that a chlorobenzene solution of 4-nitrobenzoic acid is employed in lieu of a benzene solution of 2-chloro-4-nitrobenzoic acid to obtain a 36% yield of 4′-chloro-4-nitrobenzophenone having a melting point equal to 100° C. to 101° C.

EXAMPLE 24

Preparation of 4-amino-2-chlorobenzophenone

To a solution of 2-chloro-4-nitrobenzophenone (27 grams, 0.103 mole) in hot ethanol (400 ml.) and water (200 ml.) was added iron (30 grams), followed by concentrated hydrochloric acid (25 ml.) dropwise and with stirring. After the addition, the reaction mixture was stirred at reflux during 1.5 hours, cooled, then made alkaline with ammonium hydroxide and chloroform extracted. After drying the chloroform layer (anhydrous MgSO$_4$) and filtering, the solution was evaporated to an orange solid, melting point 120° – 130° C. Crystallization from benzene-hexane gave faint yellow crystals of 4-amino-2-chlorobenzophenone having a melting point of 144° – 145° C., and recovering 16.5 grams which amounts to a 69% yield.

On analysis and calculated for $C_{13}H_{10}NOCl$ in percent: C, 67.4; H, 4.4; N, 6.1; Cl, 15.3.
Found: C, 67.6; H, 4.2; N, 6.3; Cl, 15.0.

EXAMPLE 25

Employing the procedure of Example 24 and substituting the appropriate nitrobenzophenone for 2-chloro-4-nitrobenzophenone in the reaction yielded the following aminobenzophenones as set forth in the Table II below.

TABLE II

| Aminobenzophenone | Ex. | (%) Yield | Melting Point (°C.) | Analysis (in %) Calcd. | Found |
|---|---|---|---|---|---|
| Cl—⟨⟩—CO—⟨⟩—NH$_2$ (with Cl) | 2 | 96 | 163–165 | C,58.7 H,3.4 N,5.3 Cl,26.6 | C,58.5 H,3.6 N,5.3 Cl,26.6 |
| Cl—⟨⟩—CO—⟨⟩—NH$_2$ | 3 | 63 | 183.5–184 | C,67.4 H,4.4 N,6.1 Cl,15.3 | C,67.1 H,4.5 N,6.1 Cl,15.3 |
| ⟨⟩—CO—⟨⟩ (Cl, NH$_2$) | 4 | 45 | 50–52 | N,6.1 | N,5.6 |

EXAMPLE 26

The postemergence herbicidal activity of the compounds of the present invention is demonstrated by the following tests, wherein a variety of monocotyledonous and dicotyledonous plants are treated with test compounds dispersed in aqueous-acetone mixtures. In the tests, seedling plants are grown in jiffy flats for about two weeks. The test compounds are dispersed in 50/50 acetone/water mixtures in sufficient quantity to provide the equivalent of about 0.125 to 4 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provide below. The data obtained are reported in Table III below.

Plant Species:
  MC — Annual morning-glory
  COT — cotton
  SB — sugar beet
  SOY — soybean
  COR — corn
  WO — wild oats
  BA — barnyard grass
  FOX — green foxtail
  MI — foxtail millet
  RAG — ragweed MU — mustard
LA — lambsquarters
KO — kochia

| Rating System: | % Difference in Growth from the Check* |
|---|---|
| 0 — no effect | 0 |
| 1 — possible effect | 1–10 |
| 2 — slight effect | 11–25 |
| 3 — moderate effect | 26–40 |
| 5 — definite injury | 41–60 |
| 6 — herbicidal effect | 61–75 |
| 7 — good herbicidal effect | 76–90 |
| 8 — approaching complete kill | 91–99 |
| 9 — complete kill | 100 |
| 4 — abnormal growth i.e. a definite physiological malformation but with an over-all effect less than a 5 on the rating scale. | |

*based on visual determination of stand, size, vigor chlorosis, growth malformation and over-all plant appearance.

EXAMPLE 27

The selective preemergence herbicidal activity of the compounds of the invention is exemplified by the following tests in which the seeds of a variety of monocotyledonous and dicotyledonous plants are separately mixed with potting soil and planted on top of approximately one inch of potting soil in separate pint cups. After planting, the cups are sprayed with the selected aqueous-acetone solution containing test compound in sufficient quantity to provide the equivalent of about 1 to 9 pounds per acre of test compound per cup. The treated cups are then placed on greenhouse benches and cared for in accordance with greenhouse procedures. Three weeks after treatment, the tests are terminated and each cup is examined and rated according to the rating system set forth in the previous example. The tabulated results of these tests establish the herbicidal proficiency of the test compounds and are reported in Table IV below.

TABLE III

| STRUCTURE | | ANNUAL WEEDS | | | | | | | | | CROPS | | | |
|---|---|---|---|---|---|---|---|---|---|---|---|---|---|---|
| | | KO | LA | MU | PI | Rag | BA | CR | GRF | WO | MI | COR | COT | SOY | SB |
| ⌬-CO-⌬-NH-CO-N(CH₃)₂ | 1 | 9 | 9 | 9 | 9 | 7 | 9 | 9 | 8 | | 9 | 9 | 9 | 9 |
| | 2 | 7 | 9 | 7 | 5 | 3 | 2 | 8 | 7 | | 3 | 9 | 8 | 8 |
| | 3 | 9 | 9 | 2 | 5 | 5 | 3 | 8 | 2 | | — | 8 | 3 | 8 |
| ⌬-CO-⌬-NH-CO-N(CH₃)₂ | 1 | | 9 | 9 | 9 | 9 | 1 | 2 | 1 | 1 | 0 | 0 | 2 | 9 |
| | 2 | 9 | 9 | 9 | 9 | | 1 | 1 | 1 | 0 | 0 | 1 | 1 | 9 |
| | 3 | 9 | 8 | 9 | 9 | | 1 | 1 | 0 | 0 | 1 | 1 | 1 | 9 |
| | 4 | 9 | 9 | 9 | 9 | | 1 | 1 | 0 | 0 | 0 | 0 | 9 | 9 |
| Cl-⌬-CO-⌬-NH-CO-N(CH₃)₂ | 1 | 6 | 9 | 1 | 0 | 2 | 5 | 2 | 1 | | 1 | 8 | 3 | 6 |
| | 2 | 3 | 9 | 1 | 0 | 1 | 3 | 2 | 1 | | 1 | 5 | 2 | 8 |
| | 3 | 1 | 3 | 0 | 0 | 0 | 0 | 1 | 0 | | 0 | 8 | 1 | 0 |
| Cl-⌬-CO-⌬(Cl)-NH-CO-N(CH₃)₂ | 1 | 9 | 9 | 9 | 7 | 6 | 9 | 9 | 3 | | 7 | 9 | 7 | 9 |
| | 3 | 9 | 9 | — | 7 | 7 | 9 | 8 | 3 | | 7 | 9 | 3 | 9 |
| | 4 | 9 | 9 | 9 | 9 | 7 | 8 | 9 | 3 | | — | — | — | — |
| | 5 | 9 | 9 | 8 | 3 | 6 | 2 | 9 | 3 | | — | — | — | — |
| Cl-⌬-CO-⌬-NH-CO-N(CH₃)₂ | 1 | 8 | 9 | 9 | 3 | 5 | 3 | 5 | 1 | 1 | 1 | 1 | 9 | |
| | 2 | 9 | 9 | 9 | 0 | 3 | 1 | 3 | 1 | 1 | 1 | 1 | 9 | |
| | 3 | 7 | 9 | 8 | 0 | 3 | 2 | 2 | 0 | 0 | 0 | 1 | 9 | |
| | 4 | 9 | 9 | 2 | 0 | 1 | 1 | 1 | 0 | | — | — | — | |
| ⌬-CO-⌬(Cl)-NH-CO-N(CH₃)₂ | 2 | 8 | 9 | 9 | 9 | 6 | 8 | 8 | 3 | | 9 | 9 | 8 | 9 |
| | 3 | 5 | 9 | 9 | 9 | 5 | 8 | 9 | 2 | | 7 | 9 | 8 | 9 |
| | 4 | 8 | 9 | 9 | 9 | 5 | 7 | 9 | 5 | | — | — | — | — |
| | 5 | 8 | 9 | 8 | 9 | 2 | 2 | 8 | 1 | | — | — | — | — |

TREATMENT LB/A
1  4
2  1
3  ½
4  ¼
5  ⅛

TABLE IV

| STRUCTURE | | ANNUAL WEEDS | | | | | | | | | CROPS | | | |
|---|---|---|---|---|---|---|---|---|---|---|---|---|---|---|
| | | KO | LA | MU | PI | Rag | BA | CR | GRF | WO | MI | COR | COT | SOY | SB |
| ⌬-CO-⌬-NH-CO-N(CH₃)₂ | 1 | | 7 | 9 | 5 | 9 | 3 | 7 | 1 | 0 | | | | |
| ⌬-CO-⌬-NH-CO-NH-CH₃ | 2 | 3 | 2 | 9 | 3 | 3 | 0 | 0 | 0 | 0 | | | | |
| | 3 | 0 | 0 | 8 | 0 | 3 | 0 | 0 | 0 | 0 | | | | |

TABLE IV-continued

| STRUCTURE | | KO | LA | MU | PI | Rag | BA | CR | GRF | WO | MI | COR | COT | SOY | SB |
|---|---|---|---|---|---|---|---|---|---|---|---|---|---|---|---|
| ⟨⟩—CO—⟨⟩—NH—CO—N(CH₃)₂ | 1 4 3 | 9 7 3 | 9 9 3 | 9 8 6 | 9 8 3 | 0 0 0 | 2 0 0 | 8 0 0 | 1 0 0 | 2 0 0 | 0 1 0 | 0 0 0 | 9 9 0 |
| Cl—⟨⟩—NH—CO—N(CH₃)₂  (with ⟨⟩—CO at meta) | 1 4 | 6 2 | 5 2 | 0 0 | 7 0 | 1 0 | 1 0 | 0 0 | 0 0 | 1 0 | 1 0 | 1 0 | 0 0 |
| Cl—⟨⟩—CO—⟨⟩—NH—CO—N(CH₃)₂ (Cl) | 1 4 5 | 9 6 0 | 7 6 1 | 9 9 6 | 5 0 0 | 0 0 0 | 0 0 0 | 0 0 0 | 3 0 0 | 1 0 0 | 0 0 0 | 0 0 0 | 8 3 0 |
| Cl—⟨⟩—CO—⟨⟩—NH—CO—N(CH₃)₂ | 1 4 5 | 9 8 2 | 9 7 2 | 9 5 2 | 0 0 0 | 1 0 0 | 0 0 0 | 0 0 0 | 0 0 0 | 1 0 0 | 0 0 0 | 0 0 0 | 3 7 0 |
| ⟨⟩—CO—⟨⟩—NH—CO—N(CH₃)₂ (Cl) | 1 4 5 | 9 9 1 | 9 8 0 | 9 9 3 | 7 2 0 | 1 0 0 | 6 0 0 | 2 0 0 | 0 0 0 | 0 0 0 | 0 0 0 | 0 0 0 | 9 9 2 |

TREATMENT LB/A
1. 9
2. 15
3. 5
4. 3
5. 1

I claim:
1. The compound, 3-(p-benzoyl-phenyl)-1,1-dimethyl urea.
2. The compound, 3-(m-benzoylphenyl)-1,1-dimethyl urea.
3. The compound, 3-(4-benzoyl-3-chlorophenyl)-1,1-dimethyl urea.
4. The compound, 3-[3-chloro-4-(p-chlorobenzoyl)-phenyl]-1,1-dimethyl urea.
5. The compound, 3-[p-(p-chlorobenzoyl)-phenyl]-1,1-dimethyl urea.

* * * * *